United States Patent [19]
Cordier et al.

[11] Patent Number: 4,520,665
[45] Date of Patent: Jun. 4, 1985

[54] SYSTEM FOR DETECTING A NATIVE RESERVOIR FLUID IN A WELL BORE

[75] Inventors: Bernard Cordier, Billere; Christian Berge, Morlaas, both of France

[73] Assignee: Societe Nationale Elf Aquitaine (Production), France

[21] Appl. No.: 512,365

[22] Filed: Jul. 11, 1983

[30] Foreign Application Priority Data

Jul. 13, 1982 [FR] France .................. 82 12248

[51] Int. Cl.³ .............................. E21B 47/10
[52] U.S. Cl. ................................ 73/155; 340/861; 367/85
[58] Field of Search .............. 73/151, 153, 155, 152; 340/861; 367/85

[56] References Cited

U.S. PATENT DOCUMENTS

| | | | |
|---|---|---|---|
| 2,978,634 | 4/1961 | Arps | 73/152 X |
| 3,448,611 | 6/1969 | Lebourg | 73/151 |
| 3,737,843 | 6/1973 | LePeuvedic | 367/85 |
| 3,756,076 | 9/1973 | Quichaud et al. | 73/151 |
| 3,867,714 | 2/1975 | Patton | 367/85 |
| 4,184,545 | 1/1980 | Claycomb | 367/85 X |
| 4,266,606 | 5/1981 | Stone | 73/151 X |

Primary Examiner—Jerry W. Myracle
Attorney, Agent, or Firm—Cantor and Lessler

[57] ABSTRACT

In order to detect the presence of a native reservoir fluid within a well bore, an auxiliary drilling fluid is injected into the borehole and recovered after it has circulated within the borehole. The detection system comprises a pressure-wave generator, an upstream pressure sensor for detecting the pressure wave as it passes through a first pipe in which the auxiliary drilling fluid circulates in the uncontaminated state, an outlet pressure sensor for detecting the pressure wave as it passes through a second pipe in which the auxiliary drilling fluid circulates and may be contaminated by a reservoir fluid which has entered the drilling fluid at any point of the well bore.

13 Claims, 5 Drawing Figures

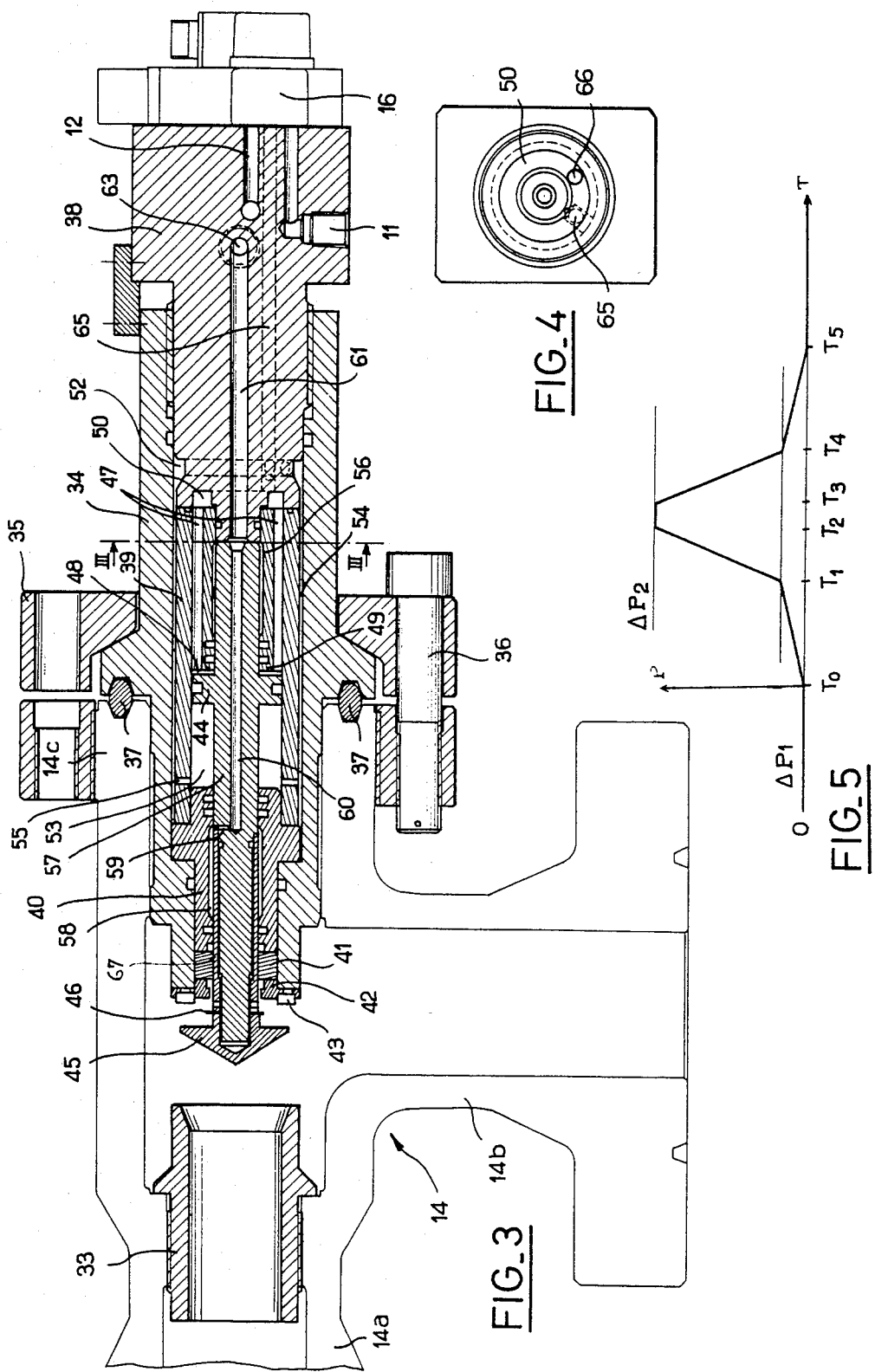

SYSTEM FOR DETECTING A NATIVE RESERVOIR FLUID IN A WELL BORE

This invention relates to a system for the detection of a native reservoir fluid and more particularly to a native reservoir gas.

While a hole is being bored by means of a drilling tool driven in rotation by means of surface or bottom-hole equipment, the drilling tool is supplied with a drilling fluid consisting, for example, of mud of known composition which serves both to cool the drilling tool and to transport cuttings from the formation which is being drilled. The drilling mud flows upwards from the bottom of the borehole to the surface via the annular space formed between the drill rods and the drilled hole or a casing string.

When a native reservoir gas such as the gas produced by the drilled formation flows into the borehole, it mixes with the drilling mud. Detection of this gas is necessary in order to guard against accidents or in order to take remedial action within the shortest possible time.

A number of detection methods and devices have been proposed and fall into two groups.

One group is concerned with surface measurements or in other words involves detection of the presence of gas by means of instruments placed at the wellhead and more precisely on the productive formation. Under these conditions, detection is carried out by measuring the level of the mud tanks (or so-called mud pits from which drilling mud is withdrawn and injected into the well and into which the mud discharged from the well is returned) since an increase in level indicates an entry of formation fluid. It is also possible to measure mud flow rates and/or mud density at the inlet and at the outlet of the borehole. Finally, the measuring instruments involve the use of the chromatographic technique.

In the event of a very high concentration of gas, as is the case when the gas enters the well abruptly and at a high rate of flow, it is possible to detect said gases by means of the measuring instruments mentioned above. However, when the concentration of gas in the drilling mud is lower or when gas entry takes place at a substantial depth, the detection means mentioned earlier react only at a very late stage, that is to say practically when the gas is close to the surface. The time allowed for taking adequate safety measures in such a case is very short and it very often happens that an accident cannot be prevented. In the case of floating instruments used in offshore drilling operations, measurements of level of mud tanks and of mud flow rate are very imprecise by reason of the movement of the drilling platform.

The second group is concerned with detection instruments placed at the bottom of the borehole, at the level of the drilling tool. These detection instruments permit highly accurate detection but are heavy and costly since they call for the use of a transmitter for conveying information from the bottom of the borehole to the surface.

The present invention relates to a system for detecting a native reservoir fluid which can be classed in the first group mentioned in the foregoing.

The method employed is of the type described in U.S. Pat. No. 4,241,123 for the detection of a native reservoir fluid in a formation to be explored. The method consists in forming at least one pressure wave in a drilling fluid which circulates within means for drilling said formation to be explored, and in measuring the time of propagation of said pressure wave between an inlet point and an outlet point of the drilling means. The inlet point corresponds to the point at which the drilling fluid is injected and therefore does not contain any trace of reservoir fluid whilst the outlet point is located on the mud return and corresponds to a point at which the velocity of the pressure wave in the drilling fluid has been modified by the reservoir fluid.

It must be understood that the expression "reservoir fluid" as used in this specification is intended to designate any fluid which may appear within a well bore and which is liable to modify the drilling fluid at a given moment and in such a manner that the velocity of the pressure wave emitted within the drilling mud is modified between the point of entry of said drilling mud into the well bore and the point of discharge of said mud from said bore.

The present invention is directed to a system for the application of the method described in the foregoing. This system essentially comprises a device for generating at least one pressure wave, means for detecting the pressure wave as it passes through a first pipe in which the auxiliary drilling fluid circulates in the uncontaminated state, means for detecting said pressure wave as it passes through a second pipe in which said drilling fluid circulates and may be contaminated by a reservoir fluid which has been introduced in said drilling fluid between the two detection means.

By virtue of the present invention, detection of a reservoir fluid such as a gas will be performed with sufficient accuracy to permit all useful safety arrangements.

Another advantage lies in the fact that the means for generating the pressure wave can be preset as a function of the rate of flow of auxiliary drilling fluid within the well bore.

A further advantage is that all the constituent elements of the detection system are readily accessible and do not entail the need for substantial equipment and/or momentary stoppage of the drilling means for maintenance of the system.

Other advantages and features of the invention will be more apparent upon consideration of the following description of a preferred embodiment of the invention, reference being made to the accompanying drawings, in which:

FIG. 3 is a sectional view of the device employed for generating pressure waves;

FIG. 4 is a sectional view of the device shown in FIG. 3, this view being taken along line III—III;

FIG. 5 is a schematic representation of a signal for controlling the piston of the device shown in FIG. 3 (pressure P as a function of time T).

Figure 1:
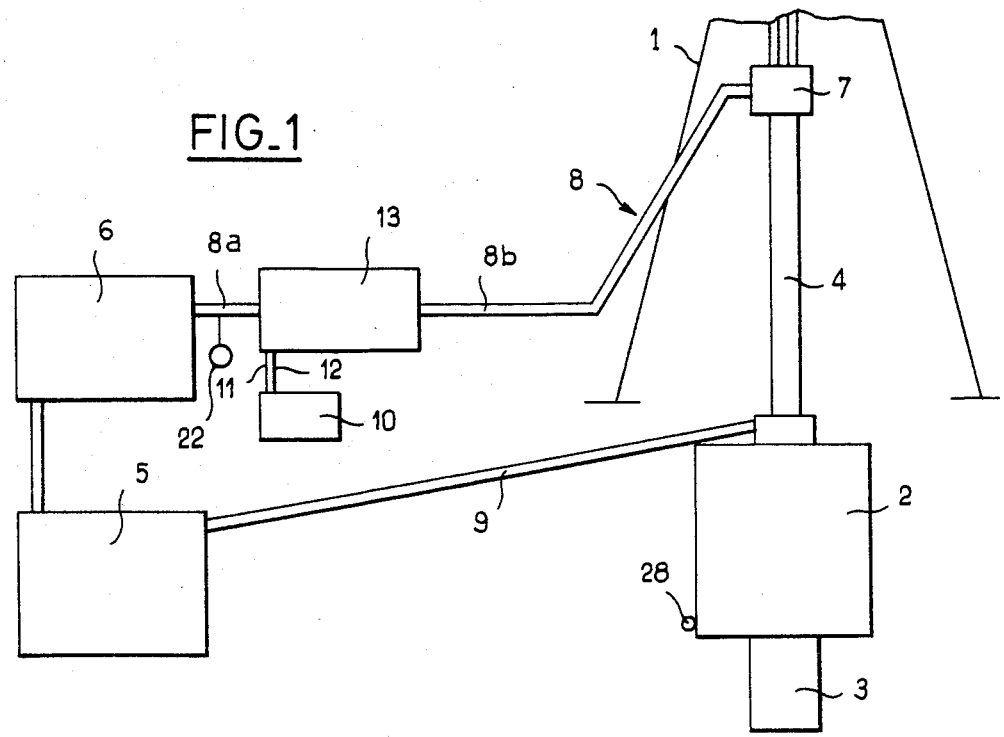
FIG. 1 is a schematic and partial diagram of a drilling rig.

A drilling rig comprises a derrick (1) in which is mounted a wellhead and the elements required for drilling. Among these elements, there are shown diagrammatically in FIG. 1 safety valves 2 mounted on an annular well gap between the casing 3 and the tubing packer 4. A drilling fluid which usually consists of mud is stored in a tank or so-called mud pit 5 from which it is withdrawn by a pump 6, then injected via a pipe 8 into an injection head 7 arranged in the derrick 1. After it has circulated within the well bore, the mud is returned to the pit 5 via a return pipe 9.

The system for detecting a reservoir fluid which may appear during a well-drilling operation comprises a hydraulic power unit 10 connected by means of a high-pressure flexible supply hose 11 and a flexible low-pressure recovery hose 12 having the same diameter to a pressure-wave device or generator 13 which is mounted on the pipe 8 between the pump 6 and the injection head 7. The pipe 8 is accordingly divided into two sections, namely an upstream section 8a and a downstream section 8b.

Figure 2:
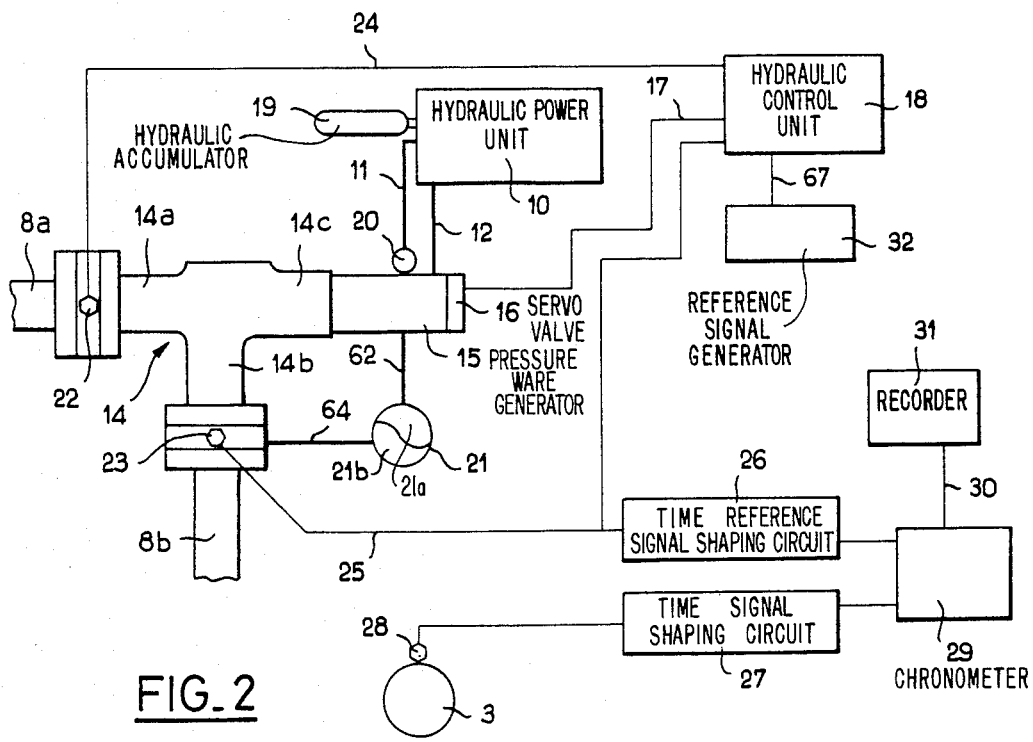
FIG. 2 is a block diagram of the detection system in accordance with the invention.

In FIG. 2, there are shown diagrammatically the principal constituent elements of the detecting system in accordance with the invention, in which the upstream section 8a is horizontal and the downstream section 8b is vertical. This arrangement, however, is shown solely for reasons of simplification and any alternative form could clearly be adopted. In particular, consideration could be given to an arrangement in which the pressure-wave generator can be mounted in a vertical position. This pressure-wave generator 13 will be described in detail hereinafter.

Between the upstream section 8a and the downstream section 8b of the pipe 8, provision is made for a stationary throttling device 33 commonly designated as a choke nipple. The nipple 33 is preferably mounted within a choke-nipple support tee 14 which constitutes an element of the generator 13. The tee 14 has three branches: a first branch 14a is connected to the upstream section 8a, the second branch 14b is connected to the downstream section 8b and the third branch 14c is connected to a mechanical device 15 for generating pressure waves. The device 15 is equipped with a servovalve 16, the construction and operation of which will not be described in detail since they are well-known to those versed in the art. One example of a suitable unit of this type is marketed by the Moog Company under the reference 73232. The servovalve 16 is connected by means of leads 17 to a hydraulic control system 18 which is also marketed by the Moog Company under the reference FO 82-310. The hydraulic power unit 10 manufactured by the Viso Company, type 3-210-30 is connected to a hydraulic accumulator 19. A filter 20 is mounted in the high-pressure line 11 in order to act as a barrier to any impurities contained in the fluid derived from the hydraulic power unit 10. A hydraulic transfer accumulator 21 of the type designated by the reference 0,5 1-400-b and marketed by the Leduc Company is mounted between the device 15 and the branch 14b of the choke-nipple support or flow tee 14. An upstream pressure sensor 22 is mounted on the upstream branch 14a whilst a downstream pressure sensor 23 is mounted on the downstream branch 14b. Said sensors 22 and 23 serve to measure the pressure difference existing within the drilling mud which circulates within the upstream branch 14a and downstream branch 14b. The sensors 22 and 23 are connected to the hydraulic control unit 18 respectively by means of leads 24 and 25. The sensors 22 and 23 can be of the type designated as TMP 13 and marketed by the Transmelec Company. The lead 25 also connects the sensor 23 to an electronic circuit 26 for shaping the time reference signal while another electronic circuit 27 is connected to a sensor 28 which constitutes the receiver for a pressure wave which propagates within the drilling means. The sensor 28 is located at the outlet point whilst the sensor 23 is located at the inlet point. The circuit 27 is also a circuit for shaping the time signal. The two circuits 26 and 27 are connected to a chronometer 29 which measures the time ΔT taken by the pressure wave to travel over the distance from the inlet sensor 23 to the outlet sensor 28. The time interval ΔT is transmitted via a lead 30 to a recorder 31. Finally, a reference signal generator 32 generates electrical pulses corresponding to the desired pressure waveform.

The device for generating the pressure waves emitted at regular intervals of time is shown in FIG. 3.

The choke nipple 33 is mounted in branch 14a of the flow tee 14 or choke support by screwing while the body 34 of the pressure-wave generating device is mounted within branch 14c of the flow tee. Said body 34 is fixed on the tee 14 by means of a fixing nut 35 and a screw 36 with interposition of O-ring seals 37. The front end of a support block 38 is inserted in the rear outer portion of the body 34 and the servovalve 16 is mounted on said support block in a suitable manner. The block 38 can be fixed within the body 34 in any desired manner and especially by screwing as shown in FIG. 3. A cylinder 39 and a front guide 40 are arranged within the body 34. By means of the front guide 40, the cylinder 39 is maintained applied against the body 34 and the block 38. A ring 41 and an outer bearing ring 42 which are held in position by screws 43 serve to maintain O-ring seals in position (not shown in the drawings). A double-acting piston 44 is placed within the cylinder 39 and this latter also serves as a rear guide for said piston 44 which is fitted with a cone-point piston-rod head 45 fitted with a braking washer 46. Provision is made in the cylinder 39 for four bores 47 for admission or discharge of oil which is supplied to an upstream chamber 48 formed between the piston 44 and an internal bearing face 49 of the cylinder 39. Said upstream chamber 48 communicates through the bores 47 with an annular chamber 50 formed in the head of the support block 38. The annular chamber 50 is supplied with pressure oil from the servovalve 16. A circular chamber 52 is formed within the head of the block 38 and communicates with a downstream chamber 53 formed behind the piston 44 via an annular gap 54 between the body 34 and the cylinder 39 and via ports 55. A rear pressure-equalizing chamber 56 is formed in the internal bearing face of the cylinder 39 whereas a front pressure-equalizing chamber 58 is formed between the front guide member 40 and the piston rod 57. The chambers 56 and 58 communicate with each other via a vertical bore 59 and a horizontal bore 60 formed in the piston rod 57. The horizontal bore 60 is aligned with a duct 61 formed within the block 38. The pressure-equalizing chambers 56 and 58 are supplied with pressure-equalizing fluid, especially with oil at a pressure equal to the pressure of the drilling mud which flows into the branch 14b of the choke-nipple support tee 14. This pressure-equalizing function is performed by the hydraulic accumulator 21, the oil-filled chamber 21a of which communicates with the duct 61 via a connecting-pipe 62 which opens into the block 38 at 63 while the mud-filled chamber 21b of said hydraulic accumulator is connected to the branch 14b of the choke support tee 14 by means of a pipe 64. Thus the pressure which prevails at each instant within the equalizing chambers 56 and 58 is equal to the pressure of mud injected into the well bore. Ducts 65 and 66 formed within the block 38 serve to connect the chamber 52 and the chamber 50 respectively to the servovalve 16. The flexible hose 12 which provides a return to the hydraulic power unit 10 in fact discharges into an oil recovery tank which is incorporated in said hydraulic power unit 10.

The displacement of the piston 44 and consequently the displacement of the cone-point piston-rod head 45 are initiated and controlled by the hydraulic control unit 18 through the servovalve 16. The motion of the piston will depend on the signal delivered by the signal generator 32 to the hydraulic control unit 18. In point of fact, since the motion of the piston 44 must not be identical irrespective of the rate of flow of mud injected into the drilling means, the signal generator 32 is provided with means (not shown) which are capable of selecting the control signal as a function of the pressure difference $\Delta P$ existing between the branches 14$a$ and 14$b$ and measured by the sensors 22 and 23. This pressure difference $\Delta P$ as well as the predetermined signal are transmitted to the inputs of a differential amplifier (not shown in the drawings but incorporated in the generator 32), the output of which is connected to the control unit 18 via a lead 67. In this manner, the cone-point head 45 will undergo a displacement in such a manner as to ensure that the pressure wave follows the shape of the signal delivered by the generator 32.

One example of a signal delivered by said generator is shown in FIG. 5. When it is decided to generate a pressure wave at a predetermined frequency within the drilling mud which is injected into the drilling means, a control signal of the type shown in FIG. 5 is delivered by the generator 32 to the hydraulic control unit 18 at the instant $T_o$, for example. Oil is then admitted within the duct 66, flows into the chamber 50, passes through the bores 47 and finally flows into the chamber 48. The oil pressure within the chamber 48 displaces the piston 44 in the direction of flow of the drilling mud in a movement such that the relative position of the cone-point head 45 with respect to the choke nipple 33 produces a reduction in cross-sectional area for the flow of drilling mud at the outlet of said choke nipple 33 and consequently produces a pressure difference $\Delta P$ which is measured by the sensors 22 and 23 and ranges from 0.1 MPa to 0.5 MPa, for example. The increase in pressure and therefore in time-duration of the corresponding displacement of the cone-point head 45 take place between the instants $T_o$ and $T_1$ with $0.1 \, s \leq T_1 - T_o \leq 5 \, s$. The cone-point head 45 subsequently continues to move towards the choke nipple 33 between the instants $T_2$ and $T_1$ until the pressure difference $\Delta P_2$ is attained with, for example, $2 \, MPa \leq \Delta P_2 \leq 5 \, MPa$ and $0.04 \, s \leq T_2 - T_1 \leq 1 \, s$. Between the instants $T_2$ and $T_3$, the cone-point head 45 is stationary with $0s \leq T_3 - T_2 \leq 5 \, s$. However, it will be readily apparent that, instead of being constant at the value $\Delta P_2$, the signal could if necessary be suitably modulated on condition that the level does not exceed the value of pressure corresponding to $\Delta P_2$.

The cone-point piston-rod head then returns to its initial position in a movement which is reverse to the preceding, as is clearly apparent from FIG. 5. This relatively slow form of reciprocating motion between $T_o$ and $T_1$ and between $T_4$ and $T_5$ is preferred to a fast return in order to avoid undue stress on moving mechanical parts and in order to prevent any shock impacts between said parts. The return movement is effected by admission of oil under pressure into the upstream chamber 53. Said oil circulates successively within the duct 65, the chamber 52, the annular gap 54 and the port 55. The equalizing pressure exerted within the chamber 58 on the rear portion of the piston rod 57 compensates for the mud pressure exerted on said piston rod at the end corresponding to the cone-point head 45. The hydraulic jack thus formed is perfectly stable without any need for control, irrespective of the mud pressure within the branch 14$b$.

Between the instants $T_1$ and $T_2$ or $T_3$ corresponding to a rapid approach of the cone-point head 45 towards the choke nipple 33, a pressure wave is then produced within the drilling mud which circulates within the flow tee. Said pressure wave propagates within the mud circuit between the inlet point corresponding to the position of the sensor 23 which delivers a signal at the moment of passage of said wave and an outlet point corresponding to the position of the sensor 28 which also delivers a signal at the moment of passage of said wave. The sensor 28 is located within a portion of the drilling means in which the drilling mud flows out of the well. Preferably, the sensor 28 is placed within the annular gap formed in the conventional manner by the inner well tubing and the outer well casing and at a distance, for example, of three meters below the level at which the mud is recovered by the pipe 9 for discharge into the mud pit 5. In fact, if no reservoir fluid such as a gas appears within the well bore, the velocity of the pressure wave in the drilling mud between the sensors 23 and 28 is not modified and the time of propagation of said wave is known and measured. On the other hand, as soon as gas mixes with the mud, the velocity of the pressure wave is accordingly modified (in the direction of a decrease in value) and the sensor 28 detects the passage of the wave at an instant of time which is different from the preceding. Measurement of the times of passage of the pressure wave generated by the cone-point piston-rod head between the sensors 23 and 28 makes it possible to follow in real time the progressive variation of the velocity characteristic in the mud between said sensors, to detect the appearance of a gas within the well bore in a very short time, and consequently to take appropriate safety measures.

As can readily be understood, it will rest with those who are versed in the art to choose those pulses and/or signals delivered by the generator which are best suited to the discharge rates of the mud pump. Similarly, in order to guard against spurious signals, the signals delivered by the sensors 23 and 28 could be passed through a filter.

The invention is clearly not limited to the embodiments of the example hereinbefore described with reference to the accompanying drawings. Depending on the applications which are contemplated, many alternative forms within the capacity of those skilled in the art may accordingly be contemplated without thereby departing either from the scope or the spirit of the invention.

What is claimed is:

1. A system for detecting a pressure wave of the type comprising means for injecting a drilling fluid, means for recovering said drilling fluid after it has circulated within a well bore, wherein said system further comprises a device for generating at least one pressure wave, means for detecting the pressure wave as it passes through a first pipe in which the auxiliary drilling fluid circulates in the uncontaminated state, means for detecting said pressure wave as it passes through a second pipe in which said drilling fluid circulates and may be contaminated by a reservoir fluid which has entered said drilling fluid at any point of the well bore.

2. A system according to claim 1, wherein the device for generating a pressure wave comprises a stationary member for throttling the flow passage provided for the drilling fluid, said throttling device being placed within the first pipe, and wherein said pressure-wave generator further comprises movable means which are placed in the flow path of the drilling fluid in the axis of said stationary throttling member and which produce a pressure wave as a result of their displacement towards said throttling member, and means for controlling the displacement of said movable means.

3. A system according to claim 2, wherein the movable means are constituted by a cone-point head mounted on a double-acting piston slidably fitted in a cylinder within which are formed two chambers on each side of said piston, and wherein the control means are hydraulic and supply said chambers with hydraulic fluid.

4. A system according to claim 1, wherein the device comprises pressure-equalizing means adapted to compensate for the pressure of drilling fluid on the double-acting piston.

5. A system according to claim 4, wherein the pressure-equalizing means are constituted by at least one annular chamber which surrounds part of the piston and into which is admitted a hydraulic fluid at an equalizing pressure equal to that of the drilling fluid.

6. A system according to claim 5, wherein said system further comprises means for controlling the equalizing pressure, said means being constituted by a hydraulic transfer accumulator comprising two chambers in leak-tight relation to each other and separated by a flexible diaphragm, one of said chambers containing a hydraulic fluid being connected to the pressure-equalizing chamber, the other chamber being connected to the downstream portion of the duct in which said stationary throttling member is fitted and being supplied with drilling fluid from said downstream portion.

7. A system according to claim 6, wherein the control means are constituted by a hydraulic power unit and a hydraulic control unit for controlling the two back-and-forth displacements of the piston as a function of the pressure difference of the auxiliary drilling fluid between two points located respectively downstream and upstream of the stationary throttling member.

8. A system according to claim 7, wherein the pressure wave is modulated as a function of said pressure difference.

9. A system according to claim 8, wherein the pressure wave is modulated in such a manner as to ensure that the amplitude increases to a slight extent during a first portion of the waveform and then increases rapidly during a second portion, and wherein the piston follows a movement which is identical with the pressure waveform during the displacement of said piston towards the stationary throttling member.

10. A system according to claim 9, wherein said system comprises a generator for producing pressure waveforms, said waveforms being preselected and a particular waveform is selected as a function of the signal received on completion of its path of travel within the mud.

11. A system for producing a pressure wave propagated in a fluid which circulates within a pipe, wherein said system comprises movable means capable of producing a reduction in cross-sectional area for the flow of said fluid within said pipe, means for displacing said movable means in a movement corresponding to a waveform selected from a number of predetermined waveforms which can be produced by a waveform generator, and a stationary throttling member placed within the pipe in such a manner as to produce a first reduction in cross-sectional area for the flow of said fluid within said pipe and consequently in order to produce a pressure difference between the upstream end and the downstream end of said stationary throttling member, the movable means aforesaid being located downstream and displaceable towards said stationary throttling member, wherein the movable means comprises a cone-point head rigidly fixed to a double-acting piston which is capable of displacement within a cylinder, two chambers being defined within said cylinder by said piston and supplied with hydraulic fluid from a hydraulic power unit, the motion of said hydraulic fluid towards and away from said power unit being dependent on a control unit connected to said power unit, said hydraulic control unit being coupled to the waveform generator in order to control the motion of the hydraulic fluid and to ensure displacement of the piston with a view to producing the waveform generated by said generator.

12. A system according to claim 11, wherein at least one pressure-equalizing chamber is formed within the cylinder and around at least part of the piston rod, said pressure-equalizing chamber being supplied with equalizing hydraulic fluid at a pressure equal to the pressure of the drilling fluid.

13. A system according to claim 12, wherein the hydraulic pressure-equalizing fluid is withdrawn from a hydraulic accumulator in which are formed two chambers separated by a flexible diaphragm, one of the chambers being filled with the pressure-equalizing fluid and connected to said pressure-equalizing chamber whilst the other chamber is filled with the fluid which circulates within the pipe downstream of the stationary throttling member in order to ensure that any pressure variation is transmitted to said pressure-equalizing fluid.

* * * * *